United States Patent [19]

Williams et al.

[11] Patent Number: 5,144,087
[45] Date of Patent: * Sep. 1, 1992

[54] PROCESS FOR THE PREPARATION OF DIBROMONITRO-ALCOHOLS AND BLENDS WITH DIBROMONITRO-ALCOHOLS

[75] Inventors: James E. Williams; Scott Thornburgh, both of West Lafayette, Ind.

[73] Assignee: Great Lakes Chemical Corp., W. Lafayette, Ind.

[*] Notice: The portion of the term of this patent subsequent to Dec. 24, 2008 has been disclaimed.

[21] Appl. No.: 777,088

[22] Filed: Oct. 16, 1991

Related U.S. Application Data

[63] Continuation of Ser. No. 631,391, Dec. 20, 1990, Pat. No. 5,075,510.

[51] Int. Cl.$^5$ .................. C07C 205/00; C07C 205/13
[52] U.S. Cl. ..................... 568/713; 568/704; 568/712
[58] Field of Search ................. 568/713, 712, 704

[56] References Cited

U.S. PATENT DOCUMENTS

| | | | |
|---|---|---|---|
| 3,658,921 | 4/1972 | Wessendorf | 568/713 |
| 3,711,561 | 1/1973 | Wessendorf | 568/713 |
| 4,723,044 | 2/1988 | Watanabe et al. | 568/713 |
| 4,922,030 | 5/1990 | Nocito et al. | 568/713 |
| 5,075,510 | 12/1991 | Williams et al. | 568/841 |

FOREIGN PATENT DOCUMENTS 0364789 4/1990 European Pat. Off. .
132549 5/1989 Japan .

OTHER PUBLICATIONS

"Nitrated Alcohols", Louis Henry, Recueil Travaux Chim Pays Bas Belgique 16, 250–252 (1987).
"Research on Mono–Carbonated Derivatives", Louis Henry, Bull. Acad. Roy. Belgique 29 (Sec. 3), 834–842 (1895).

Primary Examiner—Marianne M. Cintins
Assistant Examiner—Rebecca Cook
Attorney, Agent, or Firm—Woodard, Emhardt, Naughton Moriarty & McNett

[57] ABSTRACT

A process for preparing dibromonitro-alcohols, and mixtures thereof with bromonitro-alcohols, is disclosed in which dibromonitromethane, and optionally bromonitroethane, is reacted with a $C_1$–$C_3$ aldehyde in aqueous solution at an acid pH, preferably between about 4.0 and about 7.0. An aqueous solution of the aldehyde is prepared and the pH adjusted to the desired acid range by addition of sodium bicarbonate, and the dibromonitromethane, which may include bromonitromethane, is added thereto. The dibromonitro-alcohol product is isolated as a separate phase from the reaction mixture.

20 Claims, No Drawings

PROCESS FOR THE PREPARATION OF DIBROMONITRO-ALCOHOLS AND BLENDS WITH DIBROMONITRO-ALCOHOLS

REFERENCE TO RELATED APPLICATION

This application is a continuation in part of U.S. patent application Ser. No. 07/631,391 filed on Dec. 20, 1990, now U.S. Pat. No. 5,075,510 and entitled PROCESS FOR THE PREPARATION OF BROMONITRO-ALCOHOLS.

BACKGROUND OF THE INVENTION

1. Field of the Invention

The present invention is in the field of chemical synthesis and is directed to a method for the preparation of dibromonitro-alcohols and blends thereof with bromonitro-alcohols.

2. Description of the Prior Art

As discussed in U.S. Pat. No. 3,658,921, issued to Wessendorf, the preparation of aliphatic brominated nitro-alcohols is generally carried out in one of the following manners. The alkaline earth salt (generally sodium or calcium) of the desired nitro-alcohol is prepared from a nitro-alkane and an aldehyde with strong aqueous caustic or a metal alcoholate in alcoholic solution. By one process, the nitro-alcohol (or its metal salt) in solution is then reacted with bromine in an organic solvent such as ether, chloroform, or carbon tetrachloride. Alternatively, the salt is isolated and brominated as a suspension in an organic solvent, or is reacted with bromine in an aqueous solution by use of a phase transfer catalyst.

Several drawbacks and disadvantages are inherent in these approaches. The methods require the use of organic solvents which are either flammable, toxic, or both, and are dangerous when used in commercial scales. Isolation of the salts of the nitro-alcohols, involving the filtration and purification of said salts, is very time consuming, even in small batches. Also, the sodium salts of the nitro-alcohols are not very stable, and when exposed to air, decomposition begins even after a short time. Any heating or a slight blow can lead to a spontaneous decomposition, which may be vigorous, or even violent.

An alternate approach would involve bromination of the nitro-alkane prior to the aldol reaction. However, it is indicated in the Wessendorf patent that unsatisfactory results are obtained when bromination of the nitroparaffin is attempted prior to the reaction with the aldehyde, especially when the nitroparaffin used is nitromethane. Wessendorf states that the reaction between bromonitromethane and an aldehyde gives an unsatisfactory result, that result being a low yield.

The preparation of bromonitro-alcohols according to the Wessendorf U.S. Pat. No. 3,658,921 occurs as follows. A nitro-alkane is reacted with an aldehyde and an inorganic salt of a member of the group consisting of magnesium and alkaline earth metals in an aqueous medium to form the magnesium or alkaline earth metal salt of the nitro-alcohol. This nitro-alcohol salt is then brominated without isolation in an aqueous suspension at a temperature below 25° C.

An alternate process for preparing bromonitro-alcohols is described in U.S. Pat. No. 3,711,561, issued to Wessendorf, et al. The process of U.S. Pat. No. 3,711,561 comprises reacting a nitro-alkane with an aldehyde in an alkaline metal hydroxide in the presence of water to obtain an aqueous solution of the alkaline metal salt of the nitro-alcohol, and reacting the aqueous solution with bromine at a temperature less than 25° C. Both Wessendorf patents disclose procedures involving the isolation of the salts of the nitro-alcohols, which causes great difficulties. As indicated, the difficulties include the time-consuming filtration and purification of such salts, as well as the high instability of the salts.

In the late 1800's, M. L. Henry described the reaction of aldehydes and nitroparaffins, catalyzed by solid bases. Louis Henry, "Nitrated Alcohols", Recueil Travaux Chim Pays Bas Belgique 16, 250–252 (1897); Louis Henry, "Research on Mono-Carbonated Derivatives", Bull. Acad. Roy. Belgique 29 (Sec. 3), 834–842 (1895). His procedure entailed the admixing of the subject nitroparaffin in a solution of the aldehyde, and adding an amount of a solid base. When his experiments were duplicated in our laboratory, it was demonstrated that the method he described is undesirable for large scales due to the suddenness and intensity of the exothermic reaction. The purity of the product obtained by his method is also less than desirable.

In the Japanese Patent Application No. 1987-[Showa 62]-290,580, filed Nov. 17, 1987 (disclosed on May 25, 1989 as No. 1989-[Hei 1]-132,549), Hirahato, et al. reacted bromonitromethane with a strongly alkaline solution of formaldehyde. A consequence of their procedure is that the strongly alkaline aqueous solution of the product must be treated with sulfuric acid to prevent decomposition of the product in the alkaline medium. A result of making the solution alkaline, and its subsequent acidification, is the introduction of additional water to a system that contains a water-soluble product. Upon processing the reaction mixture by removing the water, the isolated product is contaminated by undesirable inorganic sulfate salts which are insoluble in the organic residue. A further disadvantage of this process results from the addition of the alkaline solution of this reagent aldehyde to the substrate bromonitromethane. This addition order places the halogenated nitro-alkane in a stoichiometric excess in the immediate reaction zone, a situation which favors incomplete reaction, with the concurrent formation of undesirable and hard-to-handle lachrymatory liquid monohydroxyalkylated by-products, and lowering of yields.

The preparation of halogenated nitro-alcohols is described in U.S. Pat. No. 4,922,030, issued to Nocito, et al. as follows. A halonitro-alkane is reacted with a substantially nonaqueous solution of an aldehyde, in the presence of an alkaline catalyst, to form the halonitro-alcohol. The alcohol is subsequently recovered from the reaction mixture. The Nocito, et al. patent is limited to a process involving an organic solvent and occurring at an alkaline pH.

A process for producing dibromonitro compounds is also disclosed in U.S. Pat. No. 4,723,044, which issued Feb. 2, 1988 to M. Watanabe et al. The reaction disclosed therein comprises condensing nitromethane with formaldehyde or acetaldehyde in the presence of alkali. The amount of alkali is at least 1.5 moles per mole of nitromethane. Thereafter, without isolating the product, the reaction mixture is treated with bromine, and the dibromonitro compound is recovered. See also the European Patent Application No. 0 364 789 A1, published Apr. 25, 1990.

SUMMARY OF THE INVENTION

In accordance with the present invention there is provided a novel process for the preparation of dibromonitro-alcohols, such as dibromonitroethanol, from the condensation of an aldehyde and a nitroparaffin. The dibromonitro-alcohols are prepared from nitromethane, and more specifically dibromonitromethane. Also provided is a process for preparing blends of dibromonitro-alcohols with bromonitro-alcohols from the condensation of an aldehyde and a mixture of dibromonitromethane and bromonitromethane.

It is an object of this invention to provide a novel process whereby the reaction between dibromonitromethane, and optionally including bromonitromethane, and the aldehyde is carried out in one step in an aqueous medium of acidic pH, without a phase transfer catalyst. The reaction mixture then need not be treated with a strong acid, and contamination of the product by undesirable inorganic salts is eliminated.

It is a further object of the present invention to describe a novel process whereby the reaction between dibromonitromethane, which may be blended with bromonitromethane, and a $C_1$-$C_3$ aldehyde is carried out in an acidic aqueous medium to give a maximum yield and product purity with a minimum of processing workup.

Further objects and advantages of the present invention will be apparent from the description which follows.

DESCRIPTION OF THE PREFERRED EMBODIMENT

For the purposes of promoting an understanding of the principles of the invention, reference will now be made to the preferred embodiment of the invention and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

The novel process of the present invention permits the ready preparation of a dibromonitro-alcohol of the formula

where R can be from the group of $CH_2OH$, $CH(OH)CH_3$ or $CH(OH)CH_2CH_3$. The process comprises reacting a nitro-alkane, specifically dibromonitromethane, with a $C_1$-$C_3$ aldehyde of the formula R'—CH(O), where R' is hydrogen, $CH_3$ or $CH_3CH_2$. The reaction occurs in an aqueous medium, and the product separates from the reaction media as crystals or, in the case of the higher aldehydes, an insoluble oil.

The process is also useful for preparing blends of the dibromonitro-alcohols and bromonitro-alcohols of the formula

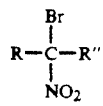

where R is as previously defined, and R" is selected from the group consisting of hydrogen, $CH_2OH$, $CH(OH)CH_3$ and $CH(OH)CH_2CH_3$. A mixture of dibromonitromethane and bromonitromethane is reacted with the $C_1$-$C_3$ aldehyde under the same conditions as indicated in the previous paragraph to yield the mixed dibromo- and bromonitro-alcohols. The product is separated from the reaction mixture in the same manner as described.

The process of the invention is based upon the unique discovery that the condensation of nitro-alkanes and aldehydes, normally run under conditions employing strong bases such as sodium hydroxide, and run at a strongly alkaline pH, can be successfully accomplished in an aqueous solution at acid pH. The process requires a minimum pH for catalysis of the reaction to occur, below which pH no reaction will occur. The minimum pH for the procedure in practice is about 4.0, and the preferred pH range for best results is about 6.0 to 7.0. This process represents an advantage over prior art methods that have employed hydroxides or alkoxides in that bromonitro-alkanes and the desired diol product have been shown to be unstable in the presence of strong bases, and may decompose, thus necessitating the need to acidify aqueous reaction mixtures before workup. The acid pH range of the present process circumvents this problem.

The procedure of this invention calls for adjusting an aqueous solution of the subtrate $C_1$-$C_3$ aldehyde to an acidic pH level by the addition of small amounts of a mild base solution such as bicarbonate of soda. The dibromonitromethane reagent, which may also include bromonitromethane, is then added, preferably at an optimized rate of addition in such a manner that the reagent is consumed immediately, but without a dangerous, rapid elevation of temperature. The need for elaborate external cooling devices is thus precluded in this way.

The need for a protracted, difficult workup of the reaction solution (as described in published procedures) is also precluded in this method, as the product separates from the aqueous solution as crystals or an insoluble oil. The development of this invention also allows the isolation of the product in higher yields and in greater purity than was previously possible, in that, in the course of removing water from the reaction mixture in other methods, undesirable inorganic salts are left in the product. In this invention, those salts are not even formed, as there is no need to acidify the reaction mixture.

The temperature of the reaction mixture is not critical to the invention, and the process may be performed at a wide range of temperatures. Preferred temperatures may be readily selected by those skilled in the art as may be desired to optimize conversion, rate of reaction, cost, convenience and the like. Typical temperatures are between about room temperature and about 45° C.

Using these improvements over other methods, the subject dibromonitro-alcohols are produced in yields in excess of 90% of the theoretical, with product purity greater than 99%. Similarly when mixtures of dibromonitromethane and bromonitromethane are used as the initial reactant, yields of the mixed dibromo- and bromonitro-alcohols are in excess of 90% and purity can exceed 99%. Thus, this process represents an improvement over prior art procedures in that it allows for the synthesis of the subject dibromonitro-alcohols, and mixtures of dibromo- and bromonitro-alcohols, in a one-step, non-violent, controllable fashion in an acidic aqueous solution using a mild base catalyst. The process operates without the aid of strong caustics, flammable or toxic organic solvents, corrosive halogen solutions, or phase transfer catalysts. Isolation of the product is accomplished without a protracted workup procedure.

The following examples illustrate the invention. The process of the invention proceeds the same for both dibromonitromethane, bromonitromethane and mixtures thereof, and works suitably with each of the $C_1$-$C_3$ aldehydes. Examples 1-6 demonstrate the general process with bromonitromethanes. Reproduction of the equivalent reactions with dibromonitromethanes yields similar results. Example 7 sets forth a procedure for preparing dibromonitroethanol, and further describes the process in respect to preparation of other dibromonitro-alcohols and blends with bromonitro-alcohols. All percentages are by weight unless otherwise indicated.

EXAMPLE 1

Preparation of 2-Bromo-2-nitropropane-1,3-diol

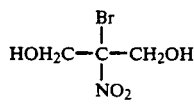

An aqueous formaldehyde solution, 37% by weight $H_2CO$, containing 75.81 g. aldehyde (0.934 mole) was adjusted to pH 6.5 with 0.5M aqueous sodium bicarbonate. The entire reactor was placed in a room temperature water bath, and 65.29 g. bromonitromethane (0.467 mole) was added, with vigorous stirring, at such a rate that the reagent was immediately consumed. Aqueous sodium bicarbonate was added to the mixture by a pH-controlled feed pump so that the reaction zone pH was constantly maintained at a level between 6.0 and 6.4. When the bromonitromethane charge was complete, the temperature of the reaction mixture was elevated to 45° C. and held there for 1-12 hours, with constant stirring. The pH of the mixture was maintained in the preset range of 6.0 to 6.5 by the pH-controlled base feed. At the end of the heated stir time, the solution was allowed to cool to room temperature, whereupon the desired product precipitated as a crystalline solid, which was isolated by vacuum filtration. The yield of product was 86.8 g. (93%), with a purity assay of 99.8% (by GC of a derivatized sample).

EXAMPLE 2

This reaction was run according to the procedure of Example 1, with the following change: the mixture was stirred at room temperature for 12 hours after the completion of the bromonitromethane charge. The yield of product ranged from 88 to 92%, with a product purity of 98.7 to 99.5%.

EXAMPLE 3

This reaction was run according to the procedure of Example 2, with the following change: the mixture was stirred at room temperature for periods of from 30 minutes to 41 hours after completion of the bromonitromethane charge. The results are shown in Table I.

TABLE I

| Stir Time | % Yield | Wt. % Assay |
| --- | --- | --- |
| 30 min | 86 | 79.1 |
| 18 hrs | 88 | 86.6 |
| 24 hrs | 93 | 99.3 |
| 41 hrs | 88 | not available |

EXAMPLE 4

This reaction was run according to the procedure of Example 3, with the following changes: the pH of the reaction zone was maintained at different pH's ranging from pH 4.0 to pH 7.0 during the bromonitromethane charge, and the mixture was stirred for 30 minutes at room temperature following reagent charge completion. The results are shown in Table II.

TABLE II

| Reaction pH | % Yield | Wt. % Assay |
| --- | --- | --- |
| 4.0 | NO REACTION | NO REACTION |
| 4.5 | 50.1 | 48.3 |
| 5.0 | 75.3 | 71.1 |
| 5.5 | 78.5 | 71.8 |
| 6.0 | 77.8 | 71.2 |
| 6.5 | 86.0 | 79.1 |
| 7.0 | 97.8 | 86.2 |

EXAMPLE 5

Preparation of 3-Bromo-3-nitropentane-2,4-diol

To 11.6 grams of acetaldehyde ($CH_3CHO$) was added dropwise an aqueous solution of sodium hydrogen carbonate until the pH of the substrate solution was 6.5. Bromonitromethane, 15.8 grams, was added dropwise to the solution at such a rate that the haloalkane did not pool in the reaction vessel, but was consumed by the reaction. The pH was maintained at 6-6.5 by addition of carbonate, as necessary. Within 30 minutes, the crude product began to separate as a yellow oil. The mixture was allowed to stir for 12 hours to ensure completeness of reaction. Upon isolation of the product, the yield was 20.85 grams (81.2% of theoretical).

EXAMPLE 6

Preparation of 1-Bromo-1-nitro-2-hydroxy-butane 6.38 grams of propionaldehyde ($CH_3CH_2CHO$) were suspended in 10 ml of water, and to the suspension was added dropwise an aqueous solution of sodium hydrogen carbonate until the pH of the substrate was 6.5. Bromonitromethane, 13.9 grams, was added dropwise at such a rate that the haloalkane did not pool in the reaction vessel, but was consumed by the reaction. The pH was maintained at 6-6.5 by addition of carbonate, as necessary. Within 30 minutes, the crude product began to separate as a yellow oil. The mixture was allowed to stir 16 hours to ensure completeness of reaction. Upon isolation of the oil, there was obtained 13.32 grams (67% yield) of the product. Extractive workup of the aqueous layer with $MeCl_2$ increased the yield to 15.88 grams (80.2%).

EXAMPLE 7

Preparation of Dibromonitroethanol from Dibromonitromethane

An aqueous formaldehyde solution, 37% by weight $H_2CO$, containing 1.48 g aldehyde, was adjusted to a pH of 6.5-7.0 with 0.5M $NaHCO_3$. A reactor containing this solution was placed in a room temperature water bath. Used as the dibromonitromethane (DBNM) reagent was a mixture assayed as 0.17% nitromethane, 13.6% bromonitromethane, 74.8% dibromonitromethane, and 11.4% tribromonitromethane. 8.78 g of the DBNM reagent, containing 6.55 g (0.029 mole) dibromonitromethane, was added dropwise to the reactor at a rate of about 0.1 ml per minute. The pH was maintained between 6.5 and 7.0 by the addition of carbonate, as necessary. At the end of the addition the temperature of the bath was elevated to 45° C. for two hours, and the bath was then allowed to cool to room temperature. The entire mixture was stirred vigorously for 16-18 hours; and the product was separated as a yellow oil with a pungent odor.

The product oil was characterized by GC, mass spec, and NMR analysis as containing bromonitropropane diol (BNPD) 5.5% by weight, dibromonitroethanol (DBNE) 59.6% by weight, and tribromonitromethane (TBNM), which does not react in this system, 34.8% by weight. The yield of product based on dibromonitromethane was 84%. When the reaction was repeated, the product consisted of 6.3% BNPD, 68.2% DBNE, and 25.5% TBNM. The yield of product, based on dibromonitromethane, was 86.7%.

As demonstrated by the foregoing example, the present process is useful in the preparation of dibromonitroalcohols from dibromonitromethane. Reaction of dibromonitromethane with acetaldehyde ($CH_3CHO$) and propionaldehyde ($CH_3CH_2CHO$), in accordance with Examples 5 and 6, yields the corresponding dibromonitro-alcohols. The foregoing reactions proceed suitably in the ranges of pH from about 4.0 to about 7.0, in accordance with Example 4. Reaction of mixtures of dibromonitromethane and bromonitromethane, as exemplified previously, proceeds in accordance with the present invention for each of the $C_1$-$C_3$ aldehydes, and in the 4-7 pH range, to yield a mixture of the corresponding dibromo- and bromonitro-alcohols. The preparation of blends of dibromo- and bromonitro-alcohols proceeds acceptably for any ratio of dibromonitromethane and bromonitromethane.

The process of this invention is a simple preparation of dibromonitro-alcohols, and optionally including bromonitro-alcohols, in an aqueous system in a controllable, non-violent reaction that is industrially very useful. The process of the invention has the advantages over currently practiced industrial technology of the avoidance of isolation of intermediates and use of dangerously flammable or toxic organic solvents. Further advantages of the invention are high yields and high purity of the products obtained, with time consuming distillations, recrystallizations, and dehydrations thereby being omitted.

In view of the above, it will be seen that the several objects of the invention are achieved and other advantageous results attained. As various changes could be made in the above process, compositions and systems without departing from the scope of the invention, it is intended that all matter contained in the above description shall be interpreted as illustrative and not in a limiting sense.

What is claimed is:

1. A process for the preparation of dibromonitro-alcohols which comprises reacting dibromonitromethane and a $C_1$-$C_3$ aldehyde in aqueous media at an acid pH of between about 4.0 and about 7.0.

2. The process of claim 1 in which the pH is between about 6.0 and about 7.0.

3. The process of claim 1 in which said reacting occurs in the absence of a phase transfer catalyst.

4. The process of claim 1 and which includes the further step of isolating the dibromonitro-alcohol as a separate phase in the reaction solution.

5. The process of claim 1 in which said reacting comprises the steps of preparing an aqueous solution of the $C_1$-$C_3$ aldehyde, adjusting the pH of the solution, and adding the dibromonitromethane to the solution.

6. The process of claim 5 in which the adjusting of the solution pH comprises adding sodium bicarbonate to the solution.

7. The process of claim 1 in which said reacting is carried out at a temperature of between about room temperature and about 45° C.

8. The process of claim 1 in which said reacting is carried out without a rapid elevation in temperature.

9. The process of claim 1 in which said reacting is carried out in the absence of external cooling devices.

10. The process of claim 1 in which said reacting is carried out at a temperature at which the dibromonitro-alcohol product is formed as a crystal or insoluble oil.

11. A process for the preparation of a mixture of dibromonitro-alcohols and bromonitro-alcohols which comprises reacting a mixture of dibromonitromethane and bromonitromethane with a $C_1$-$C_3$ aldehyde in aqueous media at an acid pH of between about 4.0 and about 7.0.

12. The process of claim 11 in which the pH is between about 6.0 and about 7.0.

13. The process of claim 11 in which said reacting occurs in the absence of a phase transfer catalyst.

14. The process of claim 11 and which includes the further step of isolating the dibromonitro-alcohol and the bromonitro-alcohol as a separate phase in the reaction solution.

15. The process of claim 1 in which said reacting comprises the steps of preparing an aqueous solution of the $C_1$-$C_3$ aldehyde, adjusting the pH of the solution, and adding the dibromonitromethane and the bromonitromethane to the solution.

16. The process of claim 15 in which the adjusting of the solution pH comprises adding sodium bicarbonate to the solution.

17. The process of claim 11 in which said reacting is carried out at a temperature of between about room temperature and about 45° C.

18. The process of claim 11 in which said reacting is carried out without a rapid elevation in temperature.

19. The process of claim 11 in which said reacting is carried out in the absence of external cooling devices.

20. The process of claim 11 in which said reacting is carried out at a temperature at which the dibromonitro-alcohol and the bromonitro-alcohol product is formed as a crystal or insoluble oil.

* * * * *